United States Patent
Kaiser et al.

(10) Patent No.: US 6,927,582 B2
(45) Date of Patent: Aug. 9, 2005

(54) METHOD AND APPARATUS FOR MONITORING THE STATE OF A CHEMICAL SOLUTION FOR DECONTAMINATION OF CHEMICAL AND BIOLOGICAL WARFARE AGENTS

(75) Inventors: Herbert J. Kaiser, Pontoon Beach, IL (US); Michael A. Centanni, Parma, OH (US)

(73) Assignee: Steris Inc., Temecula, CA (US)

( * ) Notice: Subject to any disclaimer, the term of this patent is extended or adjusted under 35 U.S.C. 154(b) by 0 days.

(21) Appl. No.: 10/900,745

(22) Filed: Jul. 28, 2004

(65) Prior Publication Data

US 2005/0001630 A1 Jan. 6, 2005

Related U.S. Application Data

(63) Continuation-in-part of application No. 10/389,036, filed on Mar. 14, 2003.

(51) Int. Cl.$^7$ .............................................. G01R 27/26
(52) U.S. Cl. ..................................................... 324/663
(58) Field of Search ...................... 422/87.01; 205/775, 205/777, 778.5, 779; 204/403.01, 431; 324/658–666; 210/96.1, 754; 436/124, 125

(56) References Cited

U.S. PATENT DOCUMENTS

| | | | |
|---|---|---|---|
| 3,636,444 A | 1/1972 | Strawn et al. ................. | 324/61 |
| 3,778,706 A | 12/1973 | Thompson .................... | 324/61 |
| 3,816,811 A | 6/1974 | Cmelik ....................... | 324/61 R |
| 4,031,742 A | 6/1977 | Michael et al. .............. | 73/40.7 |
| 4,158,810 A | 6/1979 | Leskovar .................... | 324/127 |
| 4,219,776 A | 8/1980 | Arulanandan ............... | 324/323 |
| 4,427,772 A | 1/1984 | Kodera et al. ................ | 435/27 |

(Continued)

OTHER PUBLICATIONS

U.S. Appl. No. 10/456,378, filed Jun. 6, 2003, Centanni, entitled: Method and Apparatus for Formulating and Controlling Chemical Concentrations in a Solution.

U.S. Appl. No. 10/456,380, filed Jun. 6, 2003, Centanni, entitled: Method and Apparatus for Formulating and Controlling Chemical Concentrations in a Gas Mixture.

U.S. Appl. No. 10/872,227, filed Jun. 18, 2004, Kaiser et al., entitled: Method and Apparatus for Monitoring the Purity and/or Quality of Steam.

U.S. Appl. No. 10/896,609, filed Jul. 21, 2004, Kaiser et al., entitled: Method and Apparatus for Real Time Monitoring of Metallic Cation Concentrations in a Solution.

U.S. Appl. No. 10/931,186, filed Aug. 31, 2004, Kaiser et al., entitled: Method and Apparatus for Monitoring Detergent Concentration in a Decontamination Process.

T. J. Buckley et al., "*Toroidal Cross Capacitor for Measuring the Dielectric Constant of Gases,*" Review of Scientific Instruments, vol. 71, No. 7 Jul. 2000, pp. 2914–2921.

Gross et al., "*The Dielectric Constants of Water Hydrogen Peroxide and Hydrogen Peroxide–Water Mixtures,*" L. Amer. Chem. Soc., vol. 72, 1950, pp. 2075–2080, May 1950.

(Continued)

*Primary Examiner*—Vincent Q. Nguyen
*Assistant Examiner*—Amy He
(74) *Attorney, Agent, or Firm*—Kunner & Jaffe; Michael A. Centanni

(57) ABSTRACT

A method and apparatus for monitoring the state of a chemical solution for neutralization of chemical and biological warfare agents are disclosed. A capacitor is exposed to the chemical solution, wherein the steam acts as a dielectric between the plates of the capacitor. Permittivity of the dielectric is affected by the oxidant levels in the chemical solution, and thus a measurement of electrical properties of the capacitor is used to monitor the state of the chemical solution.

14 Claims, 3 Drawing Sheets

U.S. PATENT DOCUMENTS

| | | | |
|---|---|---|---|
| 4,509,522 A | 4/1985 | Manuccia et al. | 128/634 |
| 4,525,265 A | 6/1985 | Abe et al. | 204/403 |
| 4,674,879 A | 6/1987 | Gregorig et al. | 356/301 |
| 4,769,593 A | 9/1988 | Reed et al. | 324/668 |
| 4,849,687 A | 7/1989 | Sims et al. | 324/668 |
| 4,857,152 A | 8/1989 | Armstrong et al. | 204/1 T |
| 5,151,660 A | 9/1992 | Powers et al. | 324/689 |
| 5,157,968 A | 10/1992 | Zfira | 73/149 |
| 5,171,523 A | 12/1992 | Williams | 422/20 |
| 5,243,858 A | 9/1993 | Erskine et al. | 73/204.26 |
| 5,364,510 A | 11/1994 | Carpio | 204/153.1 |
| 5,439,569 A | 8/1995 | Carpio | 204/153.1 |
| 5,459,568 A | 10/1995 | Yano et al. | 356/336 |
| 5,470,754 A | 11/1995 | Rounbehler et al. | 436/106 |
| 5,600,142 A | 2/1997 | Van Den Berg et al. | 250/339.13 |
| 5,847,276 A | 12/1998 | Mimken et al. | 73/453 |
| 5,882,590 A * | 3/1999 | Stewart et al. | 422/28 |
| 5,997,685 A | 12/1999 | Radhamohan et al. | 156/345 |
| 6,162,409 A | 12/2000 | Skelley et al. | 423/239.1 |
| 6,369,387 B1 | 4/2002 | Eckles | 250/343 |
| 6,454,874 B1 | 9/2002 | Jacobs et al. | 134/18 |
| 6,614,242 B2 | 9/2003 | Matter et al. | 324/698 |
| 6,660,231 B2 * | 12/2003 | Moseley | 422/98 |
| 6,706,648 B2 | 3/2004 | Yamazaki et al. | 438/790 |
| 2002/0014410 A1 | 2/2002 | Silveri et al. | 204/412 |
| 2002/0033186 A1 | 3/2002 | Verhaverbeke et al. | 134/26 |
| 2002/0076492 A1 | 6/2002 | Loan et al. | 427/255.28 |
| 2002/0111040 A1 | 8/2002 | Yamazaki et al. | 438/783 |
| 2002/0157686 A1 | 10/2002 | Kenny et al. | 134/1.3 |
| 2003/0063997 A1 | 4/2003 | Fryer et al. | 422/3 |
| 2003/0102007 A1 | 6/2003 | Kaiser | 134/1 |
| 2003/0157587 A1 | 8/2003 | Gomez et al. | 435/30 |
| 2004/0029257 A1 | 2/2004 | Dutil et al. | 435/266 |
| 2004/0079395 A1 | 4/2004 | Kim et al. | 134/30 |
| 2004/0178799 A1 | 9/2004 | Korenev et al. | 324/453 |
| 2004/0178802 A1 | 9/2004 | Centanni | 324/662 |
| 2004/0178803 A1 | 9/2004 | Centanni | 324/662 |
| 2004/0178804 A1 | 9/2004 | Allen et al. | 324/662 |
| 2004/0262170 A1 | 12/2004 | Centanni | 205/782 |

OTHER PUBLICATIONS

"*Humidity Sensor Theory and Behavior,*" Psychometrics and Moisture, Honeywell HVAC, Nov. 27, 2002.

Philipp, "*Charge Transfer Sensing,*" 1997. (no month available).

Wojslaw, "*Everything You Wanted to Know About Digitally Programmable Potentiometers,*" Catalyst Semiconductor, Inc., Oct. 17, 2001, Publication No. 6009.

Kittel, "*Introduction to Solid State Physics,*" Fourth Edition, John Wiley & Sons, Inc., 1971. (no month available).

Phillipp, "*The Charge Transfer Sensor,*" Sensors Magazine, Oct. 1999.

* cited by examiner

METHOD AND APPARATUS FOR MONITORING THE STATE OF A CHEMICAL SOLUTION FOR DECONTAMINATION OF CHEMICAL AND BIOLOGICAL WARFARE AGENTS

RELATED APPLICATIONS

The present invention is a Continuation-In-Part (CIP) of U.S. application Ser. No. 10/389,036, filed Mar. 14, 2003, entitled "Method and Apparatus for Measuring Chemical Concentration in a Fluid," which is incorporated herein by reference in its entirety.

FIELD OF THE INVENTION

The present invention relates generally to monitoring chemical concentrations, and more particularly to a method and apparatus for monitoring the state of a chemical solution for decontamination of chemical and biological warfare agents.

BACKGROUND OF THE INVENTION

Many chemical solutions have been developed for neutralizing chemical and biological warfare agents including, but not limited to, blister agents, nerve gas, and anthrax spores. One such chemical solution is known as Decon Green. Another chemical solution is disclosed in U.S. Pat. No. 6,245,957 to Wagner et al., issued Jun. 12, 2001, and fully incorporated herein by reference.

Decon Green is generally comprised of three components: (1) a solution of hydrogen peroxide; (2) a solution of surfactants, cosolvents and organic carbonates; and (3) an activating solution including a buffer and a molybdate.

The three primary ingredients of Decon Green are: (a) hydrogen peroxide; (b) carbonate; and (c) molybdate ion. Molybdate can be oxidized in alkaline and acidic environments to mono-, di-, tri-, and tetraperoxomolybdate. These species, in turn, release singlet oxygen quantitatively. The carbonate can be oxidized to percarbonate.

The Decon Green components may be in a powdered form for easy handling, and conveniently transfer to a contamination site for use. Powdered components may be mixed with water to produce a Decon Green chemical solution. In this regard, the components are typically mixed in a bulk tank, in a backpack sprayer, or any other convenient container. The Decon Green is then applied to the chemical and biological warfare agent contaminants. One common method of applying the Decon Green is through a spray application.

Various reactive species are formed after mixing the Decon Green components. However, over time, these reactive species decay and become inactive. Presently, there is no convenient way to determine at the point of use whether the Decon Green is in a fully active state or has decayed to an inactive state.

The present invention addresses these and other problems to provide a method and apparatus for monitoring the state of a chemical solution for decontamination of chemical and biological warfare agents.

SUMMARY OF THE INVENTION

In accordance with a preferred embodiment of the present invention, there is provided a system for monitoring oxidant levels in a chemical solution for neutralization of chemical and biological warfare agents, comprising: (a) a capacitor having first and second plates exposed to chemical solution, said chemical solution being a dielectric therebetween, wherein said capacitor has a capacitance $C_x$; and (b) processing means for determining a change in an electrical property of the capacitor, said change in the electrical property varying according to oxidant level in the chemical solution.

In accordance with another aspect of the present invention, there is provided a method for monitoring oxidant levels in a chemical solution for neutralization of chemical and biological warfare agents, the method comprising the steps of: (a) exposing a capacitor, having first and second plates, to the chemical solution, said chemical solution comprising a dielectric therebetween; and (b) determining a change in an electrical property of the capacitor, said change in the electrical property varying according to the oxidant level in the chemical solution.

An advantage of the present invention is the provision of a method and apparatus for monitoring the state of a chemical solution for decontamination of chemical and biological warfare agents, at the point of use of the chemical solution.

Another advantage of the present invention is the provision of a method and apparatus for monitoring, in situ, the state of a chemical solution for decontamination of chemical and biological warfare agents.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENTS

Figure 1:
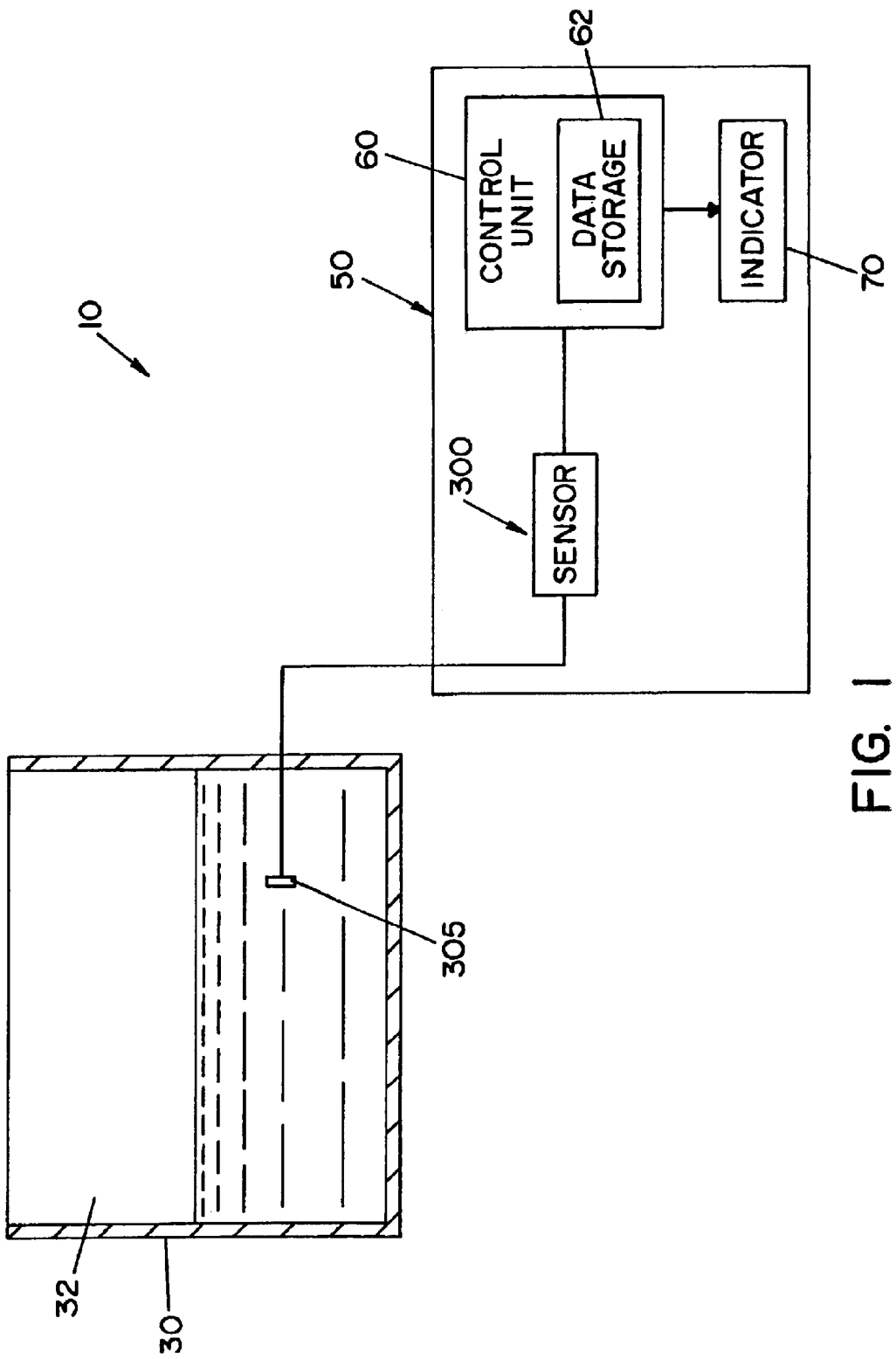
FIG. 1 is a cross-sectional side view of a container or vessel for mixing and/or storing a chemical solution for decontamination of chemical and biological warfare agents, and a block diagram of a sensing apparatus for monitoring the state of the chemical solution.

Referring now to the drawings wherein the showings are for the purpose of illustrating a preferred embodiment of the invention only, and not for the purpose of limiting same, FIG. 1 shows a system 10 comprised a container or vessel 30 suitable for mixing and/or storing a chemical solution for decontamination of chemical and biological warfare agents, and a sensing apparatus 50 for monitoring the state of the chemical solution. Vessel 30 defines a chamber 32 dimensioned to receive the chemical solution. Vessel 30 may take the form of an open or enclosed vessel. It should be understood that container or vessel 30 may include mixing means (not shown) for mixing chemical components of the chemical solution, and inlet ports (not shown) for receiving chemical components into chamber 32. Vessel 30 may also include a housing (not shown) dimensioned to receive sensing apparatus 50.

Sensing apparatus 50 is generally comprised of a control unit 60, an indicator 70, and a sensor 300. A power source (e.g., a battery) provides power to control unit 60, indicator 70 and sensor 300. Control unit 60 is preferably a microprocessor or a microcontroller. Control unit 60 also preferably includes (or is connected with) a data storage device 62 for storing data. Indicator 70 may take the form of a visual and/or an audible indicator, including, but not limited to, LEDs, LCDs, speaker, or alarm.

Figure 2:
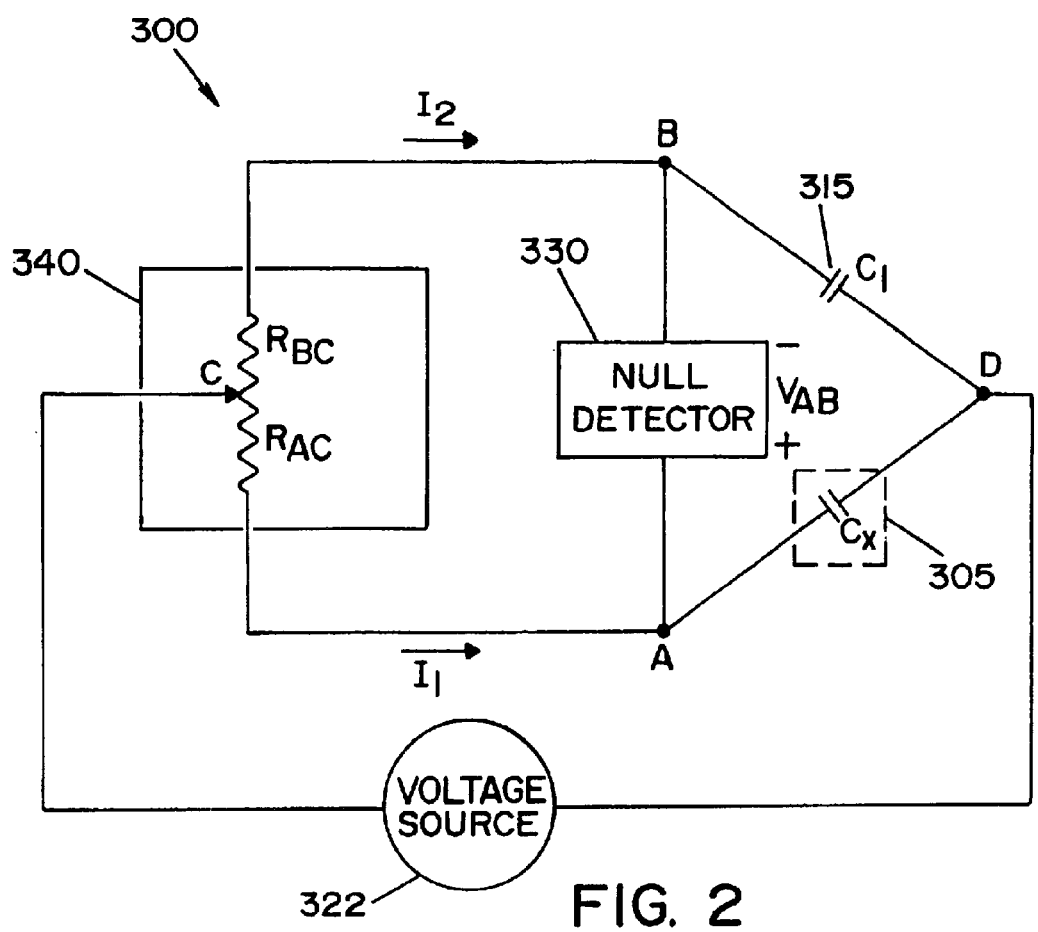
FIG. 2 is a schematic diagram of an exemplary capacitive sensor for monitoring the state of a chemical solution for decontamination of chemical and biological warfare agents, according to a first embodiment.

Sensor 300 may take the form of any suitable sensing device responsive to changes in the oxidant levels in the chemical solution for neutralization of chemical and biological warfare agents. An exemplary sensor 300, is shown in FIG. 2. Sensor 300 is described in detail in U.S. patent application Ser. No. 10/389,036, filed Mar. 14, 2003, entitled "Method and Apparatus for Measuring Chemical Concentration in a Fluid," and U.S. patent application Ser. No. 10/405,880, filed Apr. 2, 2003, entitled "Method and Apparatus for Measuring Concentration of a Chemical Component in a Gas Mixture," which are fully incorporated herein in their entirety.

Sensor 300 includes a capacitor 305 that acts as a sensing element. In one embodiment, capacitor 305 is disposed within chamber 32. Electrical properties of capacitor 305 are responsive to oxidant levels in the chemical solution inside chamber 32, as will be described in further detail below. It should be appreciated that the dielectric constant of a capacitor is dependent on its electronic "polarizability." Polarization is the ability of molecules to form a dipole under an electric field or the ability of the electric field to line up or rotate an inherent dipole, such as water molecules.

According to the embodiment illustrated in FIG. 2, sensor 300 takes the form of a "bridge circuit." As is well known to those skilled in the art, bridge circuits are used to determine the value of an unknown impedance in terms of other impedances of known value. Highly accurate measurements are possible because a null condition is used to determine the unknown impedance. The bridge circuit is used to determine a capacitance value indicative of oxidant levels in the chemical solution inside chamber 32, as will be described below.

Sensor 300 is generally comprised of a voltage source 322, a null detector 330, an electronic potentiometer 340, a capacitor 315 of a known capacitance $C_I$, and capacitor 305 having a capacitance $C_x$.

Capacitor 305 is directly exposed to the chemical solution in chamber 32. The chemical solution fills the gap between the conducting plates of capacitor 305, thereby acting as the dielectric of capacitor 305. Capacitance $C_x$ of capacitor 305 will vary in response to the oxidant levels in the chemical solution.

It should be appreciated that it may be necessary to isolate the conducting plates of capacitor 305 from the chemical solution to prevent damage to the conducting plates by the chemical components of the solution. For example, a polymeric tube may be used to isolate the chemical solution from the plates, wherein the conducting plates are located outside the tube, and the chemical solution flows through the tube. Alternatively, a polymer coating may be applied to the conducting plates.

In one embodiment, capacitor 305 is a parallel plate capacitor. However, it should be appreciated that capacitor 305 could be constructed in a different form. For example, capacitor 305 could be a cylindrical or spherical capacitor. If a spherical capacitor is used as capacitor 305, holes must be placed in the outer shell of capacitor 305 such that the chemical solution can enter and exit the capacitor. The conducting plates may be made of copper.

Electronic potentiometer 340 functions in the same manner as a mechanical potentiometer. In this regard, electronic potentiometer 340 is a three terminal device. Between two of the terminals is a resistive element. The third terminal known as the "wiper" is connected to various points along the resistive element. In the illustrated embodiment, the wiper is digitally controlled by control unit 60 (see FIG. 1). The wiper divides the resistive element into two resistors $R_{BC}$ and $R_{AC}$. Electronic potentiometer 340 may take the form of a digitally programmable potentiometer (DPPTM) available from Catalyst Semiconductor, Inc. of Sunnyvale, Calif.

In one embodiment, voltage source 322 provides an AC voltage signal, such as a sinusoidal or pulse waveform. Null detector 330 is a device for detecting a null condition (i.e., a short circuit), such as a galvanometer, a voltmeter, a frequency-selective amplifier, and the like.

Operation of sensor 300 will now be described in detail with reference to FIG. 2. The elements of the bridge circuit are connected between junctions AC, BC, AD and BD. Electronic potentiometer 340 is operated by control unit 60 to vary the resistances $R_{BC}$ and $R_{AC}$ until the potential difference between junctions A and B ($V_{AB}$) is zero. When this situation exists, the bridge is said to be balanced or is "nulled." The following relationships then hold for voltages in the main branches:

$$V_{AC}=V_{BC}, \text{ and } V_{AD}=V_{BD},$$

where $V_{AC}$ is the voltage between junctions A and C, $V_{BC}$ is the voltage between junctions B and C, $V_{AD}$ is the voltage between junctions A and D, and $V_{BD}$ is the voltage between junctions B and D. Accordingly, $$V_{AD}/V_{AC}=V_{BD}/V_{BC}$$

$$V_{AD}=V_{BD}/(V_{AC}/V_{BC})$$

Capacitor 305 of capacitance $C_x$ is connected between junctions A and D, capacitor 315 of known capacitance $C_1$ is connected between junctions B and D. Electronic potentiometer 340, connected from junction A to junction C to junction B, is adjusted by control unit 60 to vary the voltages $V_{AC}$ and $V_{BC}$.

When a null is detected by null detector 330, current $I_1$ flows from junction C to junction A to junction D, and a current $I_2$ flows from junction C to junction B to junction D. The voltage VAC across junctions A to C, and the voltage $V_{BC}$ across junctions B to C are:

$$V_{AC}=I_1R_{AC} \text{ and } V_{BC}=I_2R_{BC}.$$

The voltage across a capacitor with capacitance C, current I, and frequency is:

$$V = \frac{I}{2\pi f C}$$

Therefore, the voltages $V_{AD}$ and $V_{BD}$ may be expressed as:

$$V_{AD} = \frac{I_1}{2\pi f C_x} \quad V_{BD} = \frac{I_2}{2\pi f C_1}$$

As discussed above, $V_{AD}=V_{BD}/(V_{AC}/V_{BC})$, $V_{AC}=I_1R_{AC}$, and $V_{BC}=I_2R_{BC}$. Therefore, $$C_x = C_1\left(\frac{R_{BC}}{R_{AC}}\right).$$

In view of the forgoing relationship, when a null condition is detected, the resistance values for $R_{BC}$ and $R_{AC}$, along with the known capacitance $C_1$ of capacitor 315, can be used to determine the unknown value of capacitance $C_x$ of capacitor 305.

Differences in dipole moments of different molecules between the plates of capacitor 305 will affect the electrical properties (e.g., dielectric constant) of capacitor 305. Similarly, the presence of free charges between the plates of capacitor 305 will affect the electrical properties of capacitor 305. Changes to the electrical properties of capacitor 305 are used to monitor the state of the chemical solution. As discussed above, chemical solution fills the gap between the conducting plates of capacitor 305, thereby acting as the dielectric of capacitor 305. By configuring capacitor 305 as an element of a bridge circuit, a measure of resistance values $R_{AC}$ and $R_{BC}$, when the bridge is balanced or nulled, can be used to determine the capacitance $C_x$ of capacitor 305. The capacitance $C_x$ of capacitor 305 is indicative of the oxidant levels in the chemical solution, since the permittivity of the respective dielectric is affected by the formation and decay of peroxygen compounds in the chemical solution.

It is well known that for a parallel plate capacitor $C=(k_{\in_0})(A/d)=(\in)(A/d)$, where C is capacitance, k is the dielectric constant, $\in_0$ is the permittivity of free space ($8.85\times10^{-12}$ F/m), $\in$ is the permittivity (Farads/meter) of the capacitor dielectric, A is the area of the capacitor plates (m$^2$), and d is the separation in meters between the capacitor plates. As $\in$ increases, the capacitance C will increase. Where the capacitor is a parallel plate capacitor with circular plates of diameter D, $C=(\pi D^2\in)/(4d)$.

It will be appreciated that the dielectric constant k of the capacitor can be determined according to the following expression:

$$k = \frac{4dC}{\pi D^2 \varepsilon_0},$$

where the value of capacitance, C, is determined as discussed above. The dielectric constant of the capacitor can also be determined by determining the capacitance with the dielectric in place between the conducting plates ($C_d$), and then determining the capacitance without the dielectric in place ($C_o$). The ratio of the two capacitances equals the dielectric constant, $$k = \frac{C_d}{C_0}.$$

The response of a capacitor is influenced by the characteristics (e.g., frequency) of the AC waveform applied thereto. In this regard, capacitive reactance ($X_c$) is a function of frequency. Capacitive reactance is the opposition offered to the flow of alternating current by pure capacitance, and is expressed in ohms ($X_c=1/(2\pi f C)$). Accordingly, frequency of the waveform generated by voltage source 322 influences the response of capacitors.

Figure 3:
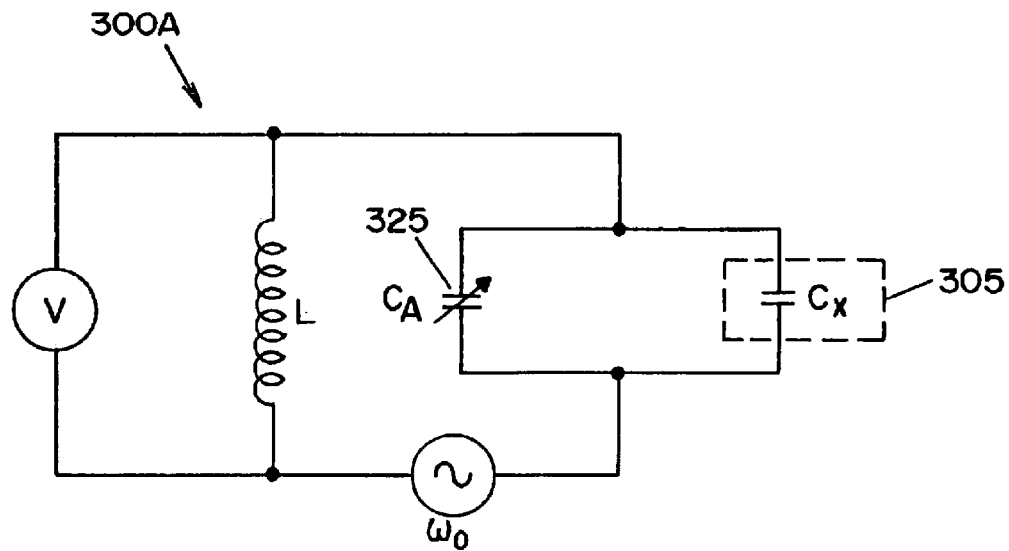
FIG. 3 is a schematic diagram illustrating an exemplary capacitive sensor for monitoring the state of a chemical solution for decontamination of chemical and biological warfare agents, according to a second embodiment.

It should be appreciated that while a preferred embodiment of the present invention includes a sensor 300 in the form of a bridge circuit, other types of circuits and techniques (including other types of bridge circuits, and capacitance meters) known to those skilled in the art, may be suitably used to measure capacitance. For example, FIG. 3 illustrates an alternative sensor 300A. Sensor 300A is an LC resonant circuit, including a variable capacitor 325 (having a capacitance $C_A$), and capacitor 305 (having a capacitance $C_x$) that acts as the sensing element, as described above. Since the resonance frequency $\omega_0=[L(C_A+C_x)]^{-1/2}$, the unknown capacitance $C_x$, of capacitor 305 can be determined.

Figure 4:
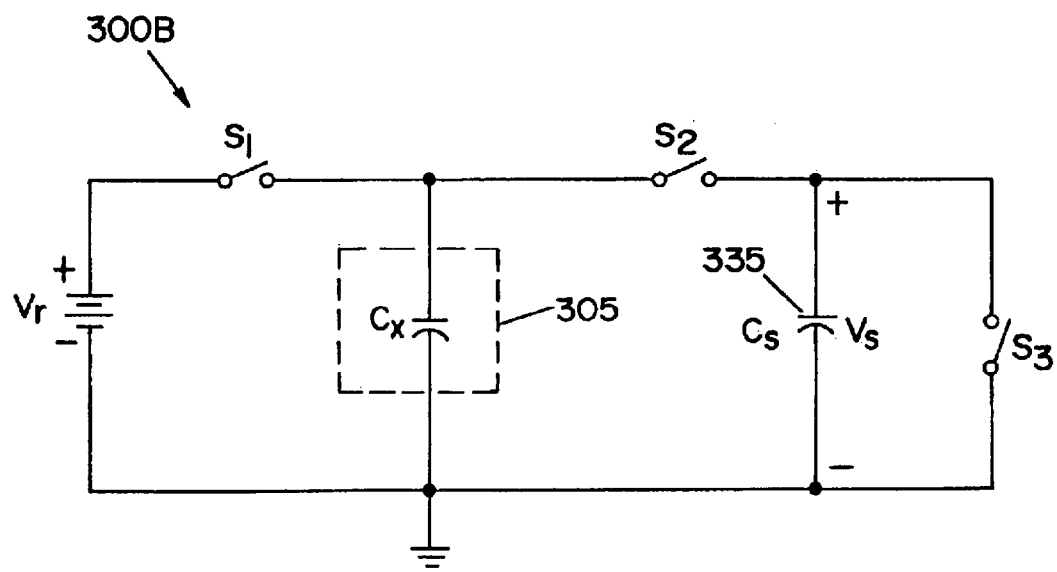
FIG. 4 is a schematic diagram illustrating an exemplary capacitive sensor for monitoring the state of a chemical solution for decontamination of chemical and biological warfare agents, according to a third embodiment.

FIG. 4 illustrates yet another alternative sensor 300B suitable for use in connection with the present invention. Sensor 300B is a "charge transfer" sensor circuit. Charge transfer sensor circuits are recognized to provide resolutions of fractions of a femtoFarad. In a charge transfer sensor circuit the unknown capacitance $C_x$, of a sense electrode is determined by charging the sense electrode to a fixed potential, and then transferring that charge to a charge detector comprising a capacitor 335 of known capacitance $C_s$. In sensor 300B, capacitor 305 of unknown capacitance $C_x$ acts as a sensing element, as described above. In this regard, chemical solution in chamber 32 fills the gap between the conducting plates of capacitor 305, thereby acting as an insulator or "dielectric" of capacitor 305. Capacitor 305 is first connected to a DC reference voltage ($V_r$) via a switch $S_1$. Switch $S_1$ is reopened after capacitor 305 is satisfactorily charged to the potential of $V_r$. Then, after as brief as possible a delay so as to minimize leakage effects caused by conductance, switch $S_2$ is closed and the charge (Q) present on capacitor 305 is transferred to capacitor 335 (i.e., the charge detector). Once the charge Q is satisfactorily transferred to capacitor 335, switch $S_2$ is reopened. By reading voltage $V_s$, the capacitance $C_x$ of capacitor 305 can be determined. $V_s$ may be input to an amplifier to provide the scaling necessary to present an analog-to-digital converter (ADC) with a useful range of voltage for digital processing. Switch $S_3$ acts as a reset means to reset the charge between charge transfer cycles, so that each charge transfer cycle has a consistent initial condition. Switches $S_1$, $S_2$ and $S_3$ may be electromechanical switches or transistors. Preferably, digital control logic is used to control switches $S_1$, $S_2$ and $S_3$. In a preferred embodiment, capacitor 335 is selected to be significantly larger than capacitor 305.

The equations governing sensor 300B are as follows:

$V_s=V_r[C_y/(C_y+C_s)]$, therefore $C_y=V_sC_s/[V_r-V_s]$.

The charge-transfer sensor has been applied in a self-contained capacitance-to-digital-converter (CDC) integrated circuit (IC). For example, Quantum Research Group produces a QProx™ CDC sensor IC (e.g., QT300 and QT301 CDC sensor ICs) for detecting femtofarad level changes in capacitance. The CDC sensor IC outputs a digital value corresponding to the detected input capacitance. The value of an external sampling capacitor controls the gain of the sensor.

Other high sensitivity circuitry is provided by such devices as the PTL 110 capacitance transducer from Process Tomography Limited of Cheshire, United Kingdom. The PTL 110 measures small values of capacitance (up to 10 picoFarads) with a resolution of 1 femtoFarad. A 1616 Precision Capacitance Bridge from IET Labs, Inc. of Westbury, N.Y., allows for measurement of capacitances in the range from 10–7 pF to 10 $\mu$F. Tektronix produces the Tektronix 130 LC Meter that measures capacitance from 0.3 pF to 3 pF. It has also been acknowledged in the prior art literature that capacitance sensor circuits using modem operational amplifiers and analog-to-digital converters (ADCs) can easily obtain resolutions to 0.01 pF.

A method of monitoring the state of a chemical solution for decontamination of chemical and biological warfare agents in chamber 32 will now be described in connection with sensor 300.

As a preliminary step, capacitor 305 is first nulled in 100% water, and a value is obtained for capacitance $C_x$ of capacitor 305 in the presence of a chemical solution having a minimum oxidant level suitable for an active state. This value for capacitance $C_x$ is then preferably stored in data storage device 62 as a setpoint value. It should be appreciated that alternative values can be used for the setpoint value including, but not limited to, a value associated with an oxidant level for an inactive state. Determination of values for $R_{AC}$ and $R_{BC}$ when the bridge is nulled can be used to determine a value for the capacitance $C_x$ of capacitor 305, since $C_x=C_1 (R_{BC}/R_{AC})$. Sensor 300 can now be used to monitor the oxidant level in the chemical solution in chamber 32, as follows.

The chemical components of the chemical solution are added and/or combined in chamber 32 of vessel 30. In the illustrated embodiment, the chemical solution for decontamination of chemical and biological warfare agents is Decon Green, as described above. The Decon Green chemical solution may be formed by combination of (1) a powdered percarbonate source including, but not limited to, percarbonate or perborate, (2) a metallic catalyst, including, but not limited to, molybdate salts, (3) a buffer to maintain appropriate pH, and (4) water. The Decon Green may also optionally include one or more of the following: builders (e.g., carbonates, silicates, etc.), corrosion inhibitors, surfactants, and an active ingredient chosen from organic/inorganic species that generate peroxo-compounds in situ. While the illustrated embodiment of the present invention is described with reference to Decon Green, it is contemplated that the present invention may also find utility in connection with other oxidative chemistries used for neutralization of chemical and biological warfare agents.

The introduction of hydrogen peroxide and the formation of the additional peroxygen compounds will result in changes to the dielectric constant of the chemical solution. The dielectric constant of the chemical solution will remain generally constant once the formation of peroxygen compounds is completed. The dielectric constant will again change as the peroxygen compounds decay.

The measured capacitance $C_x$ of capacitor 305 is compared to the setpoint value. If the measured capacitance $C_x$ differs a predetermined amount below the setpoint value, then it is determined that the chemical solution is in an inactive state, since the oxidant level is below the minimum for effective neutralization of chemical and biological warfare agents. The predetermined amount may be selected to take into consideration acceptable ranges for the oxidant level. If the measured capacitance $C_x$ is at or above the setpoint value, it is determined that the chemical solution is in an active state suitable for neutralization of chemical and biological warfare agents.

Indicator 70 may be used to provide a visual and/or audible indication of the state of the chemical solution. In this regard, indicator 70 may change state in accordance with the state of the chemical solution. For instance, a green LED may be illuminated to indicate an active state, while a red LED may be illuminated to indicate an inactive state. Alternatively, an alarm can be sounded when the chemical solution is determined to be in an inactive state. In this manner, the state of the chemical solution can be readily determined.

Furthermore, data collected by sensor 300 may be stored in data storage device 62 to provide historical data. In this regard, remaining "shelf life" of the chemical solution can be predicted from the historical data.

It should be appreciated that while a preferred embodiment of the present invention uses a measure of a capacitor's capacitance to monitor the state of the chemical solution, it is also contemplated that a measure of other electrical properties associated with a capacitor may be used to monitor the state of the chemical solution, including, but not limited to, the permittivity and dielectric constant of the capacitor dielectric.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A system for monitoring oxidant levels in a chemical solution for neutralization of chemical and biological warfare agents, comprising:

a capacitor having first and second conducting elements exposed to the chemical solution, said chemical solution being a dielectric therebetween, wherein said capacitor has a capacitance $C_x$;

processing means for determining a change in an electrical property of the capacitor, said change in the electrical property varying according to oxidant level in the chemical solution; and an indicator for indicating whether the chemical solution is in an active state having an oxidant level suitable for effective neutralization of at least one of a chemical warfare agent and a biological warfare agent, said indicator including at least one of: a visual indication means and an audible indication means.

2. A system according to claim 1, wherein said system includes a data storage device for storing a setpoint value indicative of an oxidant level of the chemical solution, said setpoint value associated with said electrical property.

3. A system according to claim 2, wherein said setpoint value is a predetermined amount from a first value indicative of an electrical property of the capacitor in the presence of the chemical solution having a minimun oxidant level for effective neutralization of at least one of a chemical warfare agent a biological warfare agent.

4. A system according to claim 2, wherein said setpoint valve is indicative of an electrical property of the capacitor in the presence of the chemical solution having a minimun oxidant level for neutralization of a least one of a chemical warfare agent and a biological warfare agent.

5. A system according to claim 1, wherein said system further comprises:

means for determining a measured value indicative of the electrical property of the capacitor as the capacitor is exposed to the chemical solution; and means for determining whether the measured value varies a predetermined amount from a setpoint value.

6. A system according to claim 1, wherein said system further comprises:
   a bridge circuit, wherein said capacitor forms a part of the bridge circuit.

7. A system according to claim 1, wherein said system further comprises:
   a charge transfer sensor circuit, wherein said capacitor forms a part of the charge transfer sensor circuit.

8. A method for monitoring oxidant levels in a chemical solution for neutralization of chemical and biological warfare agents, the method comprising:
   exposing a capacitor, having first and second conducting elements, to the chemical solution, said chemical solution comprising a dielectric therebetween;
   determining a change in an electrical property of the capacitor, said change in the electrical property varying according to the oxidant level in the chemical solution; and
   indicating by a least one of visual means and audible means whether the chemical solution is an active state having an oxidant level effective for neutralization of at least one of a chemical warfare agent and a biological warfare agent.

9. A method according to claim 8, wherein said step of determining the change in an electrical property of the capacitor includes:
   accessing pre-stored data including a setpoint value associated with said electrical property of the capacitor, wherein said setpoint value is indicative of an oxidant level of the chemical solution.

10. A method according to claim 9, wherein said setpoint value is a predetermined amount from a first value indicative of an electrical property of the capacitor in the presence of the chemical solution having a minimun oxidant level for effective neutralization of at least one of a chemical warfare agent a biological warfare agent.

11. A system according to claim 9, wherein said setpoint valve is indicative of an electrical property of the capacitor in the presence of the chemical solution having a minimun oxidant level effective for neutralization of a least one of a chemical warfare agent and a biological warfare agent.

12. A method according to claim 8, wherein said method further comprises:
   determining a measured value indicative of the electrical property of the capacitor as the capacitor is exposed to the chemical solution; and
   determining whether the measured value varies a predetermined amount from a setpoint value.

13. A method according to claim 8, wherein said capacitor forms a part of a bridge circuit.

14. A method according to claim 8, wherein said capacitor forms a part of a charge transfer sensor circuit.

* * * * *